United States Patent
Ishidai

(10) Patent No.: US 8,469,894 B2
(45) Date of Patent: Jun. 25, 2013

(54) ULTRASONIC PROBE AND ULTRASONIC DIAGNOSTIC DEVICE

(75) Inventor: Hiroshi Ishidai, Hachioji (JP)

(73) Assignee: Konica Minolta Medical & Graphic, Inc., Tokyo (JP)

( * ) Notice: Subject to any disclaimer, the term of this patent is extended or adjusted under 35 U.S.C. 154(b) by 27 days.

(21) Appl. No.: 13/146,527

(22) PCT Filed: Feb. 5, 2010

(86) PCT No.: PCT/JP2010/051688
§ 371 (c)(1),
(2), (4) Date: Jul. 27, 2011

(87) PCT Pub. No.: WO2010/092908
PCT Pub. Date: Aug. 19, 2010

(65) Prior Publication Data
US 2011/0288416 A1    Nov. 24, 2011

(30) Foreign Application Priority Data
Feb. 13, 2009   (JP) .................................. 2009-031062

(51) Int. Cl.
*A61B 9/00* (2006.01)
*B06B 1/06* (2006.01)

(52) U.S. Cl.
USPC ............ 600/459; 600/443; 600/437; 310/334

(58) Field of Classification Search
USPC ........................... 600/459, 443, 437; 310/334
See application file for complete search history.

(56) References Cited

U.S. PATENT DOCUMENTS

| | | |
|---|---|---|
| 2001/0021807 A1 | 9/2001 | Saito et al. |
| 2008/0021328 A1 | 1/2008 | Habu et al. |

FOREIGN PATENT DOCUMENTS

| | | |
|---|---|---|
| JP | 59-49754 A | 3/1984 |
| JP | 62-140451 U | 9/1987 |
| JP | 7-194517 A | 8/1995 |
| JP | 11-276479 A | 10/1999 |
| JP | 2001-276060 A | 10/2001 |
| JP | 2001-298795 A | 10/2001 |
| JP | 3280677 B2 | 2/2002 |
| JP | 3304560 B2 | 5/2002 |
| JP | 3313171 B2 | 5/2002 |
| JP | 2007-95991 A | 4/2007 |
| JP | 2008-188415 A | 8/2008 |
| WO | WO2007/145073 A1 | 12/2007 |
| WO | WO2008/010509 A1 | 1/2008 |

OTHER PUBLICATIONS

International Search Report dated Mar. 23, 2010 issued in International Appln. No. PCT/JP2010/051688.

*Primary Examiner* — Long V. Le
*Assistant Examiner* — Farshad Negarestan
(74) *Attorney, Agent, or Firm* — Holtz, Holtz, Goodman & Chick, P.C.

(57) ABSTRACT

An ultrasonic probe includes at least one transmission element layer for transmitting ultrasonic waves, at least one reception element layer for receiving ultrasonic waves and which is provided with an electrode on each of both surfaces opposed in a thickness direction thereof, and at least one matching layer for matching acoustic impedance. These layers are arranged in this order in a direction of transmitting the ultrasonic waves. An upper layer and a lower layer each sandwiching the electrodes formed on both surfaces of the reception element layer are each provided with a projecting portion which projects from the reception element layer in a direction of elevation. At least one of the electrodes formed on the reception element layer is formed by extending on a surface of one of the projecting portion opposed to a respective one of the upper layer and the lower layer.

11 Claims, 3 Drawing Sheets

ULTRASONIC PROBE AND ULTRASONIC DIAGNOSTIC DEVICE

This application is a U.S. National Phase Application under 35 USC 371 of International Application PCT/JP2010/051688 filed on Feb. 5, 2010.

FIELD OF THE INVENTION

The present invention relates to an ultrasonic probe and ultrasonic diagnostic device.

DESCRIPTION OF RELATED ART

The ultrasonic diagnostic device is an image device for medical treatment capable of minimal invasion of the tomographic image of in-vivo soft tissue from the body surface by the ultrasonic pulse reflection method. Compared with other image devices for medical treatment, this ultrasonic diagnostic device is characterized by reduced costs and an enhanced level of safety without possible exposure to X-rays and other radiation, and is capable of blood flow imaging by means of the Doppler effect. This device has been used over an extensive range covering the circulatory system (coronary artery), digestive system (stomach and intestines), internal system (liver, pancreas and spleen), urinary system (kidney and bladder) and obstetric/gynecologic system.

Since the ultrasonic probe used in the aforementioned ultrasonic diagnostic device for medical treatment is required to provide transmission/reception of ultrasonic waves of a high level of sensitivity and resolution, the probe commonly uses an inorganic piezoelectric element known under the name of PZT. In this case, a single type probe consisting of a single probe or an array type probe consisting of a two-dimensional array of a plurality of probes is often used in the oscillation mode of the piezoelectric element for transmission. The array type probe provides a high-definition image and is widely used to provide a medical image for diagnostic examination.

In the meantime, the harmonic imaging diagnosis based on the harmonic signal provides a sharp diagnostic image that cannot possibly be obtained from the conventional B-mode diagnosis, and is coming to be established as a standard diagnostic method.

Harmonic imaging provides a great number of the following advantages, as compared to imaging by fundamental waves:

1. The reduced side lobe level ensures excellent signal-to-noise ratio, hence superb contrast resolution.
2. The beam width is reduced by higher frequency, with the result that resolution in the horizontal direction is improved.
3. The sound level is smaller at a short distance, and fluctuations in sound level are smaller so that multiplex reflection does not occur.
4. The attenuation beyond the focal point is on the same level as the fundamental waves, and a high level of deep velocity can be ensured, as compared with the ultrasonic wave wherein the harmonic frequency is used as the fundamental wave.

And so on.

In a proposed structure of the array type ultrasonic probe used in harmonic imaging, the piezoelectric oscillator for transmission is separated from the piezoelectric oscillator for reception so that the operation for transmission of ultrasonic waves is different from that for reception.

The piezoelectric oscillator for reception used in such an array type ultrasonic probe is preferably capable of receiving harmonic signals at a high sensitivity. However, since the transmission frequency of the inorganic piezoelectric element depends on the thickness of the inorganic piezoelectric element, the inorganic piezoelectric element must be processed in a more compact configuration as the received frequency is higher. This has resulted in manufacturing difficulties.

To solve the aforementioned problems, the authors of the present invention have submitted a proposal method of producing a highly sensitive ultrasonic probe through the use of a highly sensitive organic piezoelectric element material, wherein a piezoelectric element for transmission is made of a single layer or laminated layers of sheet-like piezoelectric ceramics, and a sheet-like piezoelectric element for reception is formed in a single layer or laminated layers in such a way that the piezoelectric element for transmission is separate from the that for reception (Patent Literatures 1, 2 and 3).

In the meantime, it is important to find out a proper method for connection between the electrode of the piezoelectric element used in the ultrasonic probe and the wiring material. Depending on the method of connection, the quality of the signal sent from the ultrasonic probe may be deteriorated or the performance and reliability of the ultrasonic diagnostic device may be affected.

Thus, the proposals having been made so far include a method for connection wherein a lateral electrode is formed on the piezoelectric element and is connected with the lead wire (Patent Literatures 4 and 5), and a method wherein a flexible printed circuit substrate for a signal is soldered with the electrode of the piezoelectric element, and a conductive adhesive is used for connection by adhesion (Patent Literatures 6 and 7).

To downsize the ultrasonic probe, the electrode access extending from the laminated portion of the piezoelectric element is formed on the electrode laminated on both sides of the piezoelectric element, according to another disclosed document (Patent Literature 8).

EARLIER TECHNOLOGICAL LITERATURE

Patent Literature

Patent Literature 1: Unexamined Japanese Patent Application Publication No. 2008-188415
Patent Literature 2: Official Gazette of International Publication No. 2007/145073
Patent Literature 3: Official Gazette of International Publication No. 2008/010509
Patent Literature 4: Japanese Patent Application Publication No. 3313171
Patent Literature 5: Unexamined Japanese Patent Application Publication No. Hei. 7 (1995)-194517
Patent Literature 6: Japanese Patent Application Publication No. 3280677
Patent Literature 7: Unexamined Japanese Patent Application Publication No. Hei. 11 (1999)-276479
Patent Literature 8: Japanese Patent Application Publication No. 3304560

SUMMARY OF THE INVENTION

Problems to be Solved by the Invention

To ensure transmission/reception of harmonics of higher frequency, the electrode formed on the piezoelectric element must be made as thin as possible. This has made it difficult to ensure higher reliability in the connection of the piezoelectric element, electrode and wiring member in a limited space.

The space for connection with the lead wire is limited in the array type ultrasonic probe using the harmonic imaging technique. Thus, connection by lead wires as disclosed in Patent Literatures 4 and 5 will result in a poor yield rate and cannot be utilized.

There will be fluctuations in the eigen oscillation frequency and the acoustic properties will be deteriorated by using the method for direct connection between the flexible printed circuit substrate and the electrode formed on the surface of the piezoelectric element disclosed in Patent Literatures 6 and 7. This method is not suited for transmission/reception of ultrasonic waves of higher harmonics.

According to the method disclosed in Patent Literature 8, the portion from which the electrode is extended may be cracked by using a very thin metallic film to avoid adverse effect on the acoustic properties of the piezoelectric element. Especially when the portion from which the electrode is extended is bent for mounting, a crack may occur easily.

In view of the problems described above, it is an object of the present invention to provide an ultrasonic probe capable of ensuring highly reliable connection of the electrode of a piezoelectric element and a wiring member, and an ultrasonic diagnostic device equipped with this highly reliable ultrasonic probe.

Means for Solving the Problems

To solve the aforementioned problems, the present invention has the following characteristics:

1. An ultrasonic probe including: at least one transmission element layer for transmitting ultrasonic waves; at least one reception element layer receiving ultrasonic waves and providing an electrode on each of both surfaces opposed direction of a thickness; and at least one matching layer for matching acoustic impedance; and these layers being arranged in this order toward a direction of transmitting the ultrasonic waves, and wherein an upper layer and a lower layer each sandwiching the electrodes formed on both surfaces of the reception element layer are each provided with a projecting portion projecting from the reception element layer in a direction of elevation, and at least one of the electrodes formed on the reception element layer is formed by extending on a surface opposed to the upper or lower layer of the projecting portion.
2. The ultrasonic probe described in Structure 1 further including a circuit substrate forming a conductive section on a surface opposed direction of a thickness of a substrate member, wherein at least part of the circuit substrate is inserted into a concave portion surrounded by: the surface of the projecting portion of the upper layer or the electrode formed on the surface of the projecting portion of the upper layer, an end face of the reception element layer, and the surface of the projecting portion of the lower layer or the electrode formed on the surface of the projecting portion of the lower layer, and the conductive section formed on the surface of the substrate member is connected to at least one of the electrodes formed on the projecting portion of the upper or lower layer.
3. The ultrasonic probe described in Structure 1 or 2 wherein both surfaces opposed to each other in a direction of the thickness of the substrate member of a end face of the circuit substrate inserted into the concave portion is not covered with the conductive section.
4. The ultrasonic probe described in any one of the aforementioned Structures 1, 2 and 3 wherein a length of the projecting portion of the upper layer in the direction of elevation is 2% or more of the length of the upper layer in the direction of elevation, and the length of the projecting portion of the lower layer is 2% or more of a length of the lower layer in the direction of elevation; and the length of the reception element layer is 80% or more of each of the lengths of the upper and lower layers in the direction of elevation.
5. The ultrasonic probe described in any one of the aforementioned Structures 1, 2, 3 and 4 wherein a thickness of the circuit substrate with the portion of the conductive section inserted into the concave portion is 80% or more and less than 100% a thickness of the reception element layer.
6. An ultrasonic diagnostic device provided with the ultrasonic probe described in any one of the aforementioned Structures 1, 2, 3, 4 and 5.

Advantages of the Invention

According to the present invention, the upper and lower layers sandwiching the electrodes formed on both surfaces of the reception element layer are provided with projecting portions each projecting from the reception element layer in the direction of elevation, at least one of the electrodes formed on both sides is formed by extending toward the projecting portion of the upper or lower layer, and is connected to the surface opposed to the upper or lower layer. This structure provides an ultrasonic diagnostic device equipped with a highly reliable ultrasonic probe wherein the electrode of the piezoelectric element and wiring member can be connected with each other with a high level of reliability.

DETAILED DESCRIPTION OF THE PREFERRED EMBODIMENTS

Figure 1:
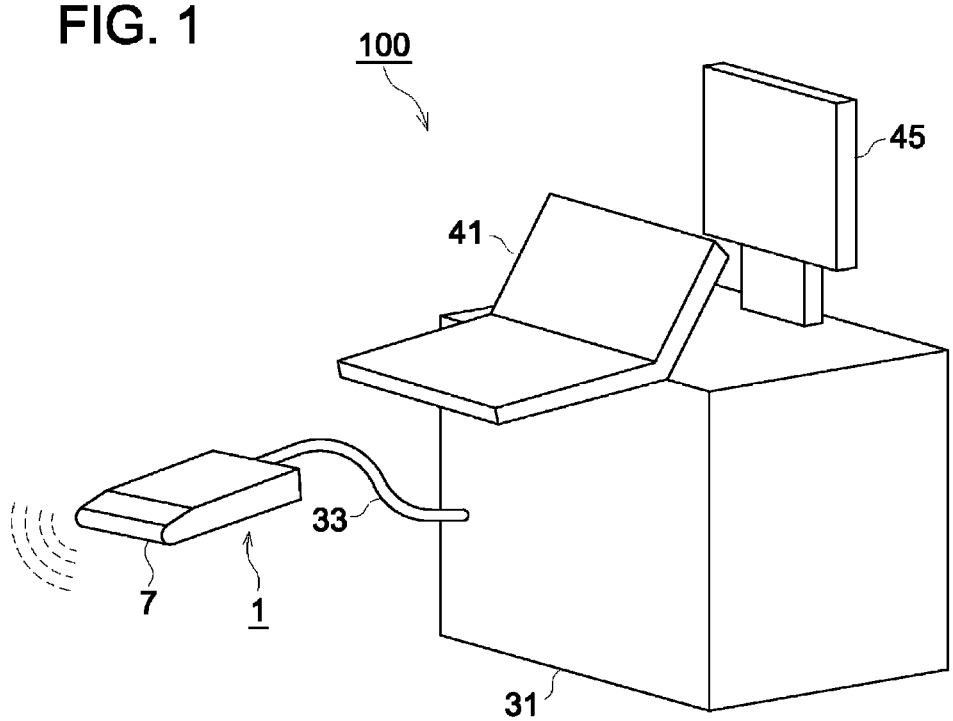
FIG. 1 is a drawing representing the external structure of the ultrasonic diagnostic device 100 in an embodiment.

The following describes an embodiment of the present invention with reference to drawings, without the present invention being restricted thereto. The same portions in the drawing assigned with the same numerals of reference will not be described to avoid duplication.

(Structures and Operations of the Ultrasonic Diagnostic Device and Ultrasonic Probe)

Figure 2:
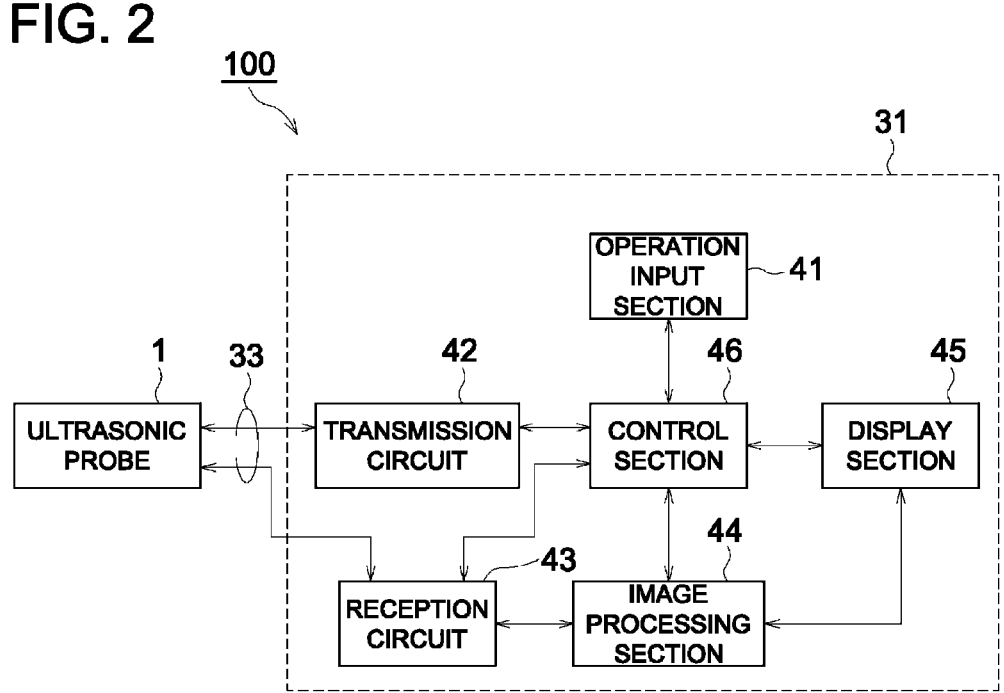
FIG. 2 is a block diagram showing the electric structure of the ultrasonic diagnostic device 100 in an embodiment.

FIG. 1 is a drawing representing the external structure of the ultrasonic diagnostic device in an embodiment. FIG. 2 is a block diagram showing the electric structure of the ultrasonic diagnostic device in an embodiment.

The ultrasonic diagnostic device 100 sends ultrasonic waves (ultrasonic signals) to the test subject such as a living body (not illustrated). From the reflection (echo, ultrasonic signal) of the ultrasonic waves reflected from the test subject having received the ultrasonic waves, the ultrasonic diagnostic device 100 forms an ultrasonic image of the internal conditions within the test subject, and displays this image on a display section 45.

The ultrasonic probe 1 sends ultrasonic waves (ultrasonic signals) to the test subject, and receives the ultrasonic waves reflected from the test subject. As shown in FIG. 2, the ultrasonic probe 1 is connected with an ultrasonic diagnostic device proper 31 through a cable 33, and is electrically connected with the transmission circuit 42 and reception circuit 43.

In response to the control section 46, the transmission circuit 42 sends electric signals to the ultrasonic probe 1 through the cable 33, and ensures that ultrasonic waves are sent from the ultrasonic probe 1 to the test subject.

In response to the instruction from the control section 46, the reception circuit 43 receives from the ultrasonic probe 1 through the cable 33 the electric signal in conformance to the reflection of the ultrasonic waves coming from inside the test subject.

In response to the instruction of the control section 46, based on the electric signal received by the reception circuit 43, the image processing section 44 forms an image of the internal conditions of the test subject as an ultrasonic image.

The display section 45 is made up of a liquid crystal display panel and others. In response to the instruction of the control section 46, the display section 45 displays the ultrasonic image formed by the image processing section 44.

The operation input section 41 consists of a switch, key substrate and others, and is provided to allow a user to input the command for specifying the start of diagnosis or the data including the individual information on a test subject.

The control section 46 is made up of a CPU, memory and others. According to the procedure programmed on the basis of the input on the operation input section 41, the control section 46 controls various parts of the ultrasonic diagnostic device 100.

Figure 3:
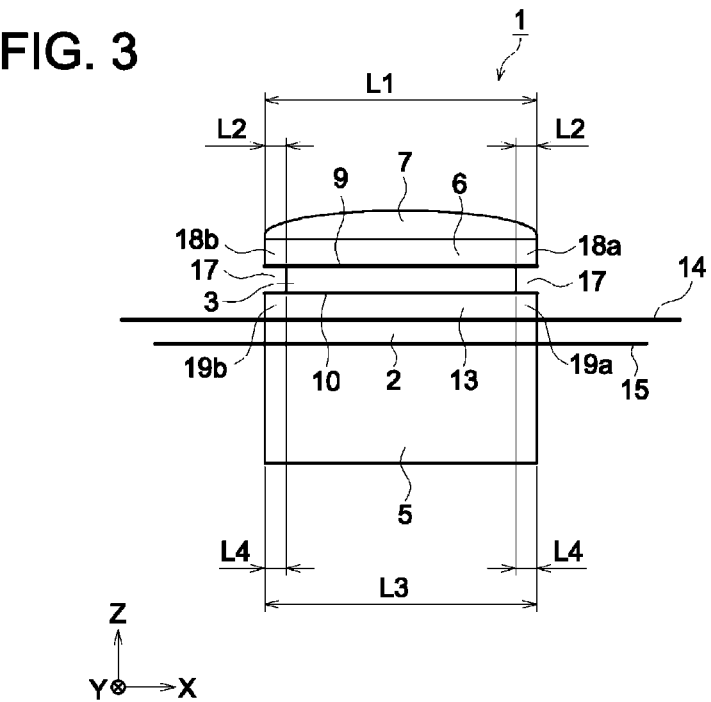
FIG. 3 is a cross sectional view representing the structure of the head of the ultrasonic probe in a first embodiment.

FIG. 3 is a cross sectional view representing the structure of the head of the ultrasonic probe in a first embodiment.

The following description is given with reference to the coordinates of X, Y and Z in the drawing: It should be noted that the X-axis direction indicates the direction of elevation (direction of dicing), and the Z-axis positive direction denotes the direction wherein ultrasonic waves are sent. The Z-axis direction represents the direction of lamination. The following description of various parts will be given in the order of laminates.

In the ultrasonic probe 1 of FIG. 1, the fourth electrode 15, transmission element layer 2, third electrode 14, intermediate layer 13, second electrode 10, reception element layer 3, first electrode 9, matching layer 6, and acoustic lens 7 are laminated in that order on the packing material 5.

The transmission element layer 2 is a piezoelectric element composed of an inorganic material such as PZT (lead zirconate titanate). A third electrode 14 and fourth electrode 15 are mounted on both surfaces opposed direction of a thickness. The transmission element layer 2 is approximately 320 µm thick.

The third electrode 14 and fourth electrode 15 are connected to the cable 33 by means of a connector (not illustrated), and are further linked to the transmission circuit 42 through the cable 33. It is also possible to make such arrangements that, if electric signals are inputted into the third electrode 14 and fourth electrode 15, ultrasonic waves are sent in the Z-axis positive direction from the transmission element layer 2.

The third electrode 14 and fourth electrode 15 are approximately 1 to 2 µm thick. The thickness of the third electrode 14 and fourth electrode 15 is preferably minimized from the viewpoint of acoustics. If the thickness is excessively reduced, however, cracks will occur to the electrode and reliability will be lost. This thickness is preferably kept in the range of 0.1 to 10 µm, preferably in the range of 0.1 to 5 µm. Especially the thickness of the fourth electrode 15 from which ultrasonic waves are sent is preferably minimized for the purpose of maintaining good acoustic properties.

In the third electrode 14 and fourth electrode 15, such a metallic material as gold, silver and aluminum is used to form a film on both surfaces of the transmission element layer 2 by means of vapor deposition method or photolithography.

The intermediate layer 13 is made of a resin material. The intermediate layer 13 connects the second electrode 10 and third electrode 14, and absorbs the oscillation of the reception element layer 3 to ensure that the transmission element layer 2 will not be oscillated by resonance when the reception element layer 3 has received the ultrasonic waves reflected by the test subject.

The resin material used for the intermediate layer 13 is exemplified by polyvinyl butyral, polyolefin, polyacrylate, polyimide, polyamide, polyester, polysulfone, epoxy, and oxetane. Further, these resins can be mixed with fine particulates for adjustment of the properties thereof.

The thickness of the intermediate layer 13 is selected in conformance to the desired sensitivity and frequency characteristics. For example, the thickness is approximately in the range of 180 to 190 µm. Depending on the desired sensitivity and frequency characteristics, the intermediate layer 13 can be omitted.

The reception element layer 3 is composed of a plurality of piezoelectric elements that contain organic piezoelectric materials.

The organic piezoelectric material used to form the reception element layer 3 is exemplified by vinylidene fluoride polymer. Other examples of the organic piezoelectric material include the copolymer based on vinylidene fluoride (VDF). This vinylidene fluoride copolymer is a copolymer between vinylidene fluoride and other monomers. Other monomers include ethylene trifluoride (TrFE), tetrafluoroethylene (TeFE), perfluoroalkylvinylether (PFA), perfluoroalkoxyethylene (PAE) and perfluorohexanone ethylene.

Generally, the piezoelectric element of the inorganic piezoelectric material is capable of receiving only the ultrasonic waves in the frequency band equivalent to about twice the frequency of the fundamental waves. By contrast, the piezoelectric element made of organic piezoelectric material is capable of receiving the ultrasonic waves in the frequency band equivalent to about four through five times the frequency of the fundamental waves, and is therefore suited for increasing the bandwidth of the received frequency. The ultrasonic waves are received by an organic piezoelectric element 21 capable of receiving the ultrasonic waves over a wide frequency range, and therefore, the ultrasonic probe 1 and ultrasonic diagnostic device 100 having a simple structure in the present invention provide an increased frequency bandwidth.

The thickness of the reception element layer 3 can be set as appropriate, in conformance to the frequency of the ultrasonic waves to be received, or the type of the organic piezoelectric material. For example, when the ultrasonic waves having a center frequency of 15 MHz are to be received, the thickness of the reception element layer 3 is approximately in the range of 35 to 40 µm.

In such a reception element layer 3, a film of a prescribed thickness is formed by flow-casting from the solution of the organic piezoelectric material. This is heated and crystallized, and is formed into a sheet having a prescribed size.

The first electrode 9 and second electrode 10 are formed on both surfaces opposed to each other direction of a thickness of the reception element layer 3 (in the Z-axis direction), respectively.

The thickness of the first electrode 9 and second electrode 10 are approximately in the range of 1 to 2 μm. The electrode of the reception element layer 3 is preferably minimized from the viewpoint of acoustics. If the thickness is excessively reduced, however, cracks will occur to the electrode and reliability will be lost This thickness is preferably kept in the range of 0.1 to 10 μm, preferably in the range of 0.1 to 5 μm. The reception element layer 3 receives the ultrasonic waves of high frequency. Accordingly, both the first electrode 9 and second electrode 10 are preferably minimized from the viewpoint of acoustics.

Such a metallic material as gold, silver and aluminum is used to form a film on the first electrode 9 and second electrode 10 by means of the vapor deposition method or photolithography. The electrode to be used for the reception element layer 3, especially the first electrode 9, must be formed in a very thin configuration to ensure reception of ultrasonic waves with high sensitivity. Thus, highly conductive gold is preferably used as a metallic material.

The first electrode 9 and second electrode 10 are connected with the reception circuit 43 through the cable 33.

When the reception element layer 3 has received the ultrasonic waves reflected by the test subject, and is oscillated, an electric signal occurs to the piezoelectric element between the first electrode 9 and second electrode 10 in conformance to the reflected waves. The electric signal having occurred between the first electrode 9 and second electrode 10 is received by the reception circuit 43 through the cable 33 and is formed into an image by the image processing section 44.

The matching layer 6 has an intermediate impedance of the acoustic impedances of various layers, and provides matching of acoustic impedances. The present embodiment illustrates an example wherein the matching layer 6 is a single layer. This is also applicable to the case of multiple layers. In a single layer, the thickness of the matching layer 6 is approximately 140 μm, for example.

The acoustic lens 7 is composed of silicone and resin and is used to converge the transmitted or received ultrasonic waves into a prescribed distance.

A transmission element layer 2 wherein the third electrode 14 and fourth electrode 15 are formed, an intermediate layer 13, a reception element layer 3 wherein the first electrode 9 and second electrode 10 are formed, and a matching layer 6 are adhered onto the packing material 5 in that order by an adherent, as shown in FIG. 3. After lamination, dicing is performed in the X-axis direction opposite the ultrasonic wave emission, starting from the matching layer 6. Dicing is performed further in the Z-axis negative direction, from the adhesive layer of the packing material and fourth electrode. After the groove formed by dicing has been filled with the silicone and other resins, an acoustic lens 7 is adhered onto the topmost layer.

In the present invention, the matching layer 6 is the upper layer sandwiching the first electrode 9 and second electrode 10 formed on the reception element layer 3, and the intermediate layer 13 corresponds to the lower layer. The matching layer 6 and intermediate layer 13 are provided with the projecting portions 18a and 18b projecting from the reception element layer 3, and the projecting portions 19a and 19b, as shown in FIG. 3.

The first electrode 9 is formed by extending up to the surface opposed to the intermediate layer 13 of the projecting portions 18a and 18b. The second electrode 10 is formed by extending up to the surface opposed to the matching layer 6 of the projecting portions 19a and 19b.

The following describes the method for forming the first electrode 9 by extending up to the surface opposed to the intermediate layer 13 of the projecting portions 18a and 18b.

Such a metallic material as gold, silver and aluminum is used to form a metallic thin film in advance on the portions of at least the projecting portions 18a and 18b in the surface opposed to the first electrode 9 of the matching layer 6, by means of the vapor deposition method or photolithography.

In a lamination process to be performed later, the first electrode 9 formed on the reception element layer 3 and the metallic thin film formed on the matching layer 6 are connected by means of a conductive adherent and others. Then the first electrode 9 is extended up to the projecting portions 18a and 18b.

The same procedure can be used to form the second electrode 10 by extending up to the surface opposed to the matching layer 6 of the projecting portions 19a and 19b.

Such a metallic material as gold, silver and aluminum is used to form a metallic thin film as an electrode in advance on the portions of at least the projecting portions 19a and 19b in the surface opposed to the second electrode 10 of the intermediate layer 13, by means of the vapor deposition method or photolithography. In a lamination process to be performed later, the second electrode 10 formed on the reception element layer 3 and the metallic thin film formed on the matching layer 6 are connected by means of a conductive adherent and others. Then the second electrode 10 is extended up to the projecting portions 19a and 19b.

The present embodiment will be described with reference to an example wherein the projecting portions 18a and 18b and projecting portions 19a and 19b are formed on both surfaces of the reception element layer 3. The present invention is not restricted thereto. The projecting portions can be formed on one of these surfaces. In the following description, for the items common to both the projecting portions 18a and 18b and projecting portions 19a and 19b, there will be no distinction between "a" and "b". Thus, the description will be "projecting portion 18" or "projecting portion 19" without "a" or "b".

L1 is the length of the matching layer 6 in the direction of elevation (in the X-axis direction); L3 is the length of the intermediate layer 13 in the direction of elevation (in the X-axis direction); L2 is the length of the projecting portion 18 projecting from the end face of the reception element layer 3 in the direction of elevation (in the X-axis direction); and L4 is the length of the projecting portion 19 in the direction of elevation (in the X-axis direction). The present embodiment will be described below on the assumption that L1=L3 and L2=L4.

The concave portion 17 is surrounded by the first electrode 9 formed on the projecting portion 18, the end face of the reception element layer, and the second electrode 10 formed on the projecting portion 19. As will be described below, a circuit substrate is inserted into the concave portion 17 and is connected with the first electrode 9 and second electrode 10.

Figure 4:
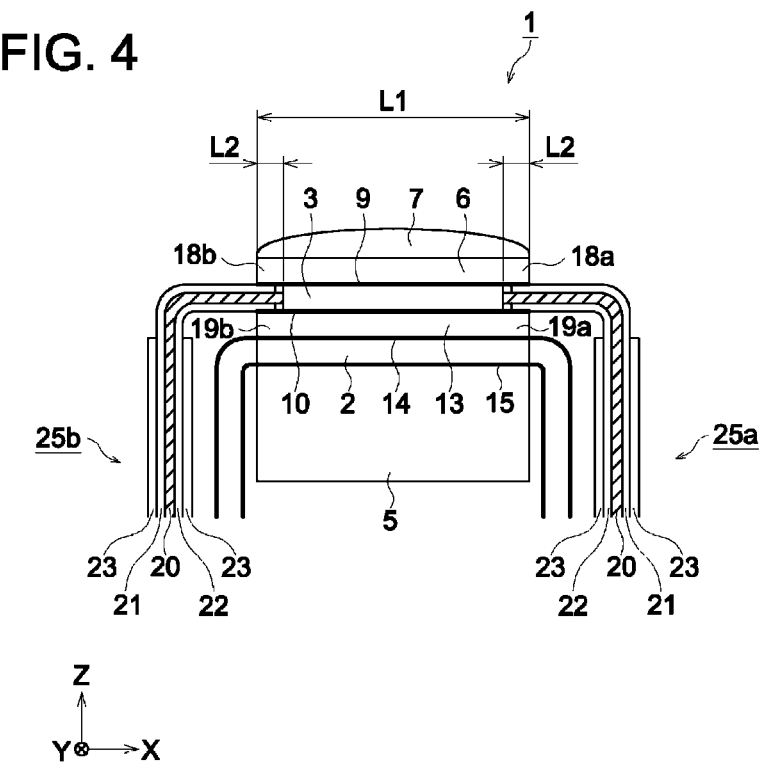
FIG. 4 is a cross sectional view illustrating the connection between the concave portion 17 and circuit substrate 25 in the first embodiment.
Figure 5:
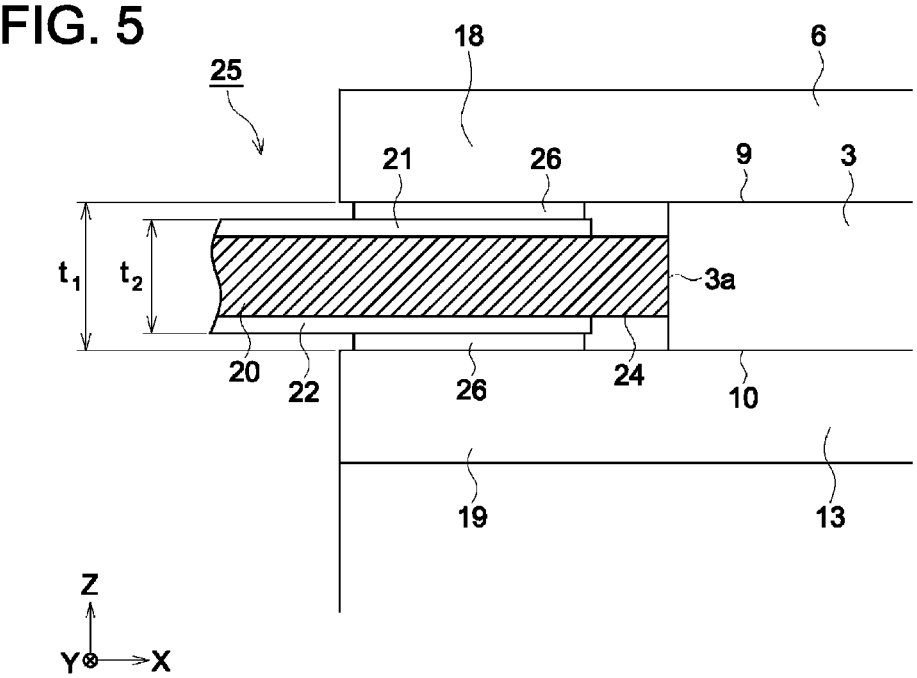
FIG. 5 is a enlarged view of the cross section of the circuit substrate 25 inserted into the concave portion 17.

Referring to FIGS. 4 and 5, the following describes an example of connecting the first electrode 9 and second electrode 10 formed on both sides of the concave portions 17, with the circuit substrate 25.

FIG. 4 is a cross sectional view illustrating the connection between the concave portion 17 and circuit substrate 25 in the first embodiment FIG. 5 is an enlarged view of the cross section of the circuit substrate 25 inserted into the concave portion 17.

The circuit substrate 25 is a double-faced substrate wherein conductive sections 21 and 22 made of copper foil are formed on both surfaces of the substrate material 20 consisting of polyimide. As shown in FIGS. 4 and 5, part of the circuit substrate 25 is inserted into the concave portion 17, and the conductive portions 21 and 22 formed on both surfaces of the substrate material 20 are connected to the first electrode 9 and second electrode 10, respectively, by the adhesive member 26 such as a conductive adhesive.

As described above, in the present embodiment, the first electrode 9 is formed on the projecting portion 18, while the second electrode 10 is formed on the surface of the projecting section 19. This structure provides easy connection by insertion of the circuit substrate 25 into the concave portion 17, and eliminates the possibility of the first electrode 9 and second electrode 10 being cracked by vibration after connection. This structure enhances the reliability of the ultrasonic diagnostic device 100.

The interval P between the first electrode 9 and second electrode 10 in the Y-axis direction subsequent to dicing is extremely small If the wiring pattern of the portion connected to the first electrode 9 and second electrode 10 of the circuit substrates 25a and 25b is formed at an equally spaced interval, mounting difficulties will occur. In the present embodiment, the interval of the pattern of the portion to be connected with the first electrode 9 and second electrode 10 of the circuit substrates 25a and 25b (not illustrated) is set at 2P, a doubled value, in such a way that the patterns of the circuit substrates 25a and 25b in the Y-axis direction will be connected with the electrodes provided on both sides of the reception element layer 3, alternately.

In the present invention, the first electrode 9 formed on the concave portion 17 is connected with the conductive portion 21, and the second electrode 10 is connected with the conductive portion 22, using the double-faced flexible substrate, whereby high-density mounting is achieved.

In addition to the double faced flexile substrate, a single faced flexible substrate and other wiring materials can be used for connection between the first electrode 9 and second electrode 10. It is also possible to arrange such a structure that the first electrode 9 is formed on the surface of any one of the projecting portions 18a and 18b, and the second electrode 10 is formed on the surface of any one of the projecting portions 19a and 19b.

As shown in FIG. 5, the both ends that are opposed to the end face 24 of the circuit substrate 25 along the thickness are not covered with the projecting portions 21 and 22. This arrangement prevents the projecting portion 22 from electrically conducting with the end face 3a, even if the end face 24 has been inserted until it abuts on the end face 3a of the reception element layer 3. This ensures easy mounting.

The length L2 of the projecting portions 18a and 18b projecting from the end face of the reception element layer 3 in the direction of elevation (in the X-axis direction) is preferably set at 2% or more of the length L1 of the matching layer 6 as the upper layer in the direction of elevation. Further, the length L4 of the projecting portions 19a and 19b projecting from the end face of the reception element layer 3 in the direction of elevation (in the X-axis direction) is preferably set at 2% or more of the length L3 of the intermediate layer 13 as the lower layer in the direction of elevation.

If L2 and L4 are below 2% of L1 and L3, there will be insufficiency in the area of connection between the projecting portions 21 and 22, and the first electrode 9 and second electrode 10. This may result in misalignment or defective conduction due to vibration, and will lead to a sudden increase in rejection rates.

If the length L2 of the projecting portions 18a and 18b in the direction of elevation and the length L4 of the projecting portions 19a and 19b in the direction of elevation are excessive, the length of the reception element layer 3 in the direction of elevation will be insufficient, as compared with the external shape of the ultrasonic probe, whereby efficiency will be deteriorated. To avoid this, the lengths of the projecting portions 18 and 19 are preferably determined in such a way that the length of the reception element layer 3 will be 80% or more of any one of the lengths of the matching layer 6 and intermediate layer 13 in the direction of elevation.

The "t1" of FIG. 5 indicates the thickness of the reception element layer 3 and "t2" represents the thickness of the circuit substrate 25 including the conductive portions 21 and 22. t2 is preferably 80% or more through 100% exclusive of t1. If t2 is below 80% of t1, there will be an increase in the amount of the adhesive member 26 to be loaded, and this will involve assembling difficulties. If t2 is greater than 100% of t1, the circuit substrate 25 cannot be inserted in position and the adhesive member 26 cannot be loaded.

The present embodiment has been described with reference to the example of the procedure wherein projecting portions 18 and 19 are arranged on the upper and lower layers of the reception element layer 3, and the circuit substrate 25 is inserted into the concave portion 17 for connection. The third electrode 14 and fourth electrode 15 of the transmission element layer 2 can be connected with the circuit substrate, using the same procedure. To be more specific, projecting portions are formed on the intermediate layer 13 as the upper layer of the transmission element layer 2 and the packing material 5 as the lower layer, and the third electrode 14 and fourth electrode 15 are formed on the opposing surfaces of the projecting portions, respectively. Then the circuit substrate is inserted into the projecting portions. This procedure ensures easy connection of the third electrode 14 and fourth electrode 15 with the circuit substrate.

Figure 6:
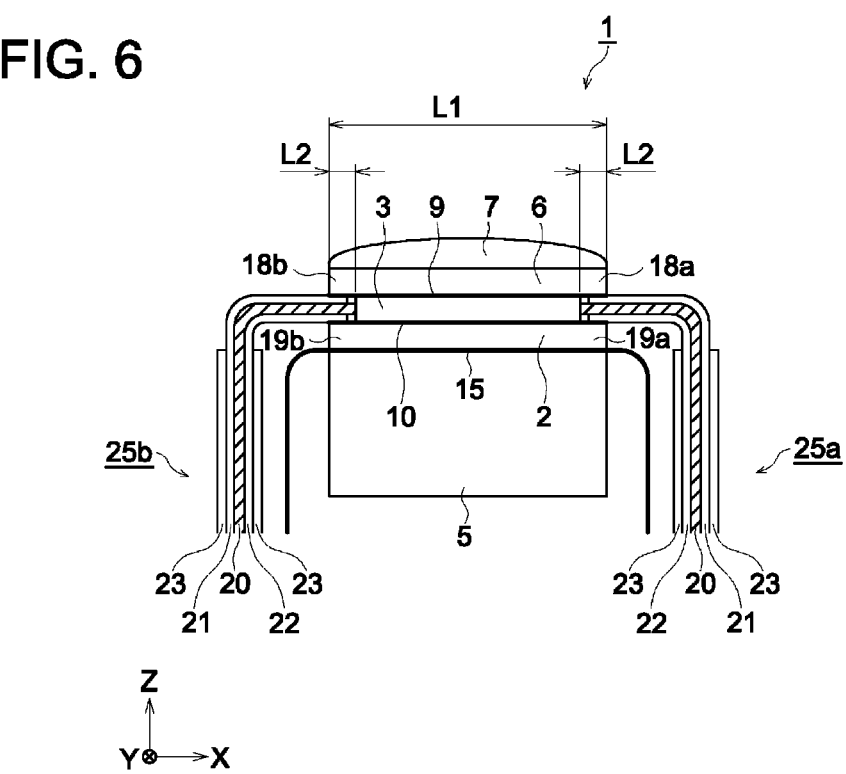
FIG. 6 is a cross sectional view illustrating the connection between the reception element layer 3 and flexible substrate in a second embodiment.

The second embodiment shows an example of the present invention being applied to the ultrasonic probe 1 devoid of an intermediate layer 13, as shown in FIG. 6. FIG. 6 is a cross sectional view illustrating the connection between the reception element layer 3 and flexible substrate in a second embodiment.

In the ultrasonic probe 1 of FIG. 6, a fourth electrode 15, transmission element layer 2, second electrode 10, reception element layer 3, first electrode 9 matching layer 6 and acoustic lens 7 are laminated in that order on the packing material 5.

The third electrode 14 and intermediate layer 13 are omitted. The second electrode 10 serves as a common electrode for both the transmission element layer 2 and reception element layer 3.

In the present embodiment, the matching layer 6 is an upper layer for sandwiching the first electrode 9 and second electrode 10 formed on the reception element layer 3. The transmission element layer 2 is a lower layer. The matching layer 6 and transmission element layer 2 are provided with the projecting portions 18 and 19 projecting from the reception element layer 3.

The first electrode 9 and second electrode 10 are formed by extending up to the projecting portions 18 and 19, respectively, and are respectively bonded onto the surfaces wherein the matching layers 6 of the projecting portions 18 and 19 are opposed to the transmission element layer 2.

The present embodiment will also be described with reference to an example wherein the projecting portions 18 and 19 are provided on both sides of the reception element layer 3, without the present invention being restricted thereto. For example, the projecting portions 18 and 19 may be provided on one of the sides of the reception element layer 3.

In FIG. 6, similar to the case of the first embodiment, the circuit substrate 25 is inserted into the concave portion surrounded by the first electrode 9 formed on the surface of the projecting portion 18, the end face of the transmission element layer and the second electrode 10 formed on the surface of the projecting portion 19 for connection with the first electrode 9 and second electrode 10.

Thus, the present invention is also applicable to the ultrasonic probe 1 devoid of an intermediate layer 13.

EXAMPLES

The following describes the examples used to verify the effects of the present invention, without being restricted thereto.

Example 1

A hundred ultrasonic probes 1 having a structure shown in FIG. 3 were manufactured by changing the length of the reception element layer 3 in the direction of elevation (in the X-axis direction). These ultrasonic probes 1 were connected to the circuit substrates 25 to test the reliability, as shown in FIG. 4.

The following describes the procedure of manufacturing the ultrasonic probe 1.

The transmission element layer 2 made of PZT was finished by lapping to produce a sheet having a length of 10 mm in the X-axis direction (L3), a length of 55 mm in the Y-axis direction and a length (thickness) of 320 μm in the Z-axis direction.

Gold was coated by the vapor deposition method on both surfaces of the transmission element layer 2 to produce a third electrode 14 and fourth electrode 15 having a thickness of 0.3 μm method.

Polyvinyl butyral was used as a material to produce an intermediate layer 13 having a length (L4) of 10 mm in the X-axis direction, a length of 55 mm in the Y-axis direction, and a length (thickness) of 185 μm in the Z-axis direction. After that, gold or aluminum was coated by the vapor deposition method on the surface of the intermediate layer 13 wherein the intermediate layer 13 and reception element layer 3 were in contact to ensure that the surface resistance would not exceed 20 ohms Then a second electrode 10 having a thickness of 0.3 μm was manufactured.

To produce the reception element layer 3, the copolymer powder of vinylidene polyfluoride (with a weight average molecular weight of 290,000) was dissolved into the nine-to-one mixture solvent consisting of the ethyl methyl ketone (hereinafter referred to as MEK) and dimethyl formaldehyde (hereinafter referred to as DMF) heated to 50 degrees Celsius, wherein the aforementioned copolymer powder consisted of the mole fraction of the vinylidene fluoride (hereinafter referred to as VDF) and trifluoroethylene (hereinafter referred to as 3FE) at the ratio of 75 to 25. The solution obtained by this procedure was flow-cast on a glass plate. After that, the solvent was dried at 50 degrees Celsius to produce a film (organic piezoelectric material) having a melting point of 155 degrees Celsius and a thickness of approximately 140 μm.

This film was drawn to 400 percent at room temperature by a single-screw drawing machine equipped with a load cell capable of measuring the load applied to the chuck. The tension in the axial direction of drawing at the end of 400-percent drawing was 2.2 N per unit width (mm) With the drawn length kept unchanged, the drawing machine was heated, and heat treatment was conducted at 135 degrees Celsius for one hour. After that, cooling was conducted to reduce the temperature down to the room temperature, while the distance between chucks was kept controlled so that the tension would not be reduced to zero. The film having been heat-treated and obtained in this procedure had a thickness of 40 μm.

After that, the length in the Y-axis direction was kept constant at 55 mm, while the length in the X-axis direction was changed in seven levels; 9.7, 9.62, 9.6, 9.0, 8.0, 7.8 and 7.0 mm, whereby a sheet-like film was formed. Then gold or aluminum was coated on both sides of this film in a vapor deposition method so that the surface resistance did not exceed 20 ohms This procedure produced a test sample equipped with surface electrodes (first electrode 9 and second electrode 10) having a thickness of 0.3 μm on both sides.

This is followed by the step of polarizing these electrodes at room temperature by application of 0.1 Hz AC voltage. Polarization was performed at a low voltage. Voltage was gradually applied so that the electric field between electrodes would be 100 MV/m in the final phase. The final amount of polarization was calculated from the residual amount of polarization when the piezoelectric material was regarded as a capacitor, namely, the film thickness, electrode area and the cumulate amount of electric charge with respect to the applied electric field, whereby the organic piezoelectric materials of the aforementioned dimensions were obtained.

Gold or aluminum was coated on the surface of the projecting portion 18 in contact with the reception element layer of the projecting portion 18 in a vapor deposition method so that the surface resistance did not exceed 20 ohms This step produced a first electrode 9 having a thickness of 0.3 μm.

The transmission element layer 2 with the third electrode 14 and fourth electrode 15 formed thereon, the intermediate layer 13, the reception element layer 3 with the first electrode 9 and second electrode 10 formed thereon, and the matching layer 6 were bonded in that order on the packing material 5, using an adherent. Then lamination was formed so that L2=L4, as shown in FIG. 3. After lamination, dicing was performed in the direction opposite the emission of ultrasonic waves from the matching layer 6. Then dicing was performed further to a depth of 100 μm in the Z-axis direction from the bonded layers of the packing material and 4th electrode.

In the final phase, an acoustic lens 7 formed of silicone is bonded on the topmost layer to produce the heads of ultrasonic probes 1 having seven different lengths of the reception element layer 3 in the X-axis direction.

The circuit substrate 25 used in this test is the double-faced flexible substrate consisting of the polyimide-made substrate material 20 having a thickness of 20 μm, and the organic piezoelectric elements 21 and 22 made of copper foil having a thickness of 9 μm, respectively. Accordingly, the circuit substrate 25 containing the organic piezoelectric elements 21 and 22 has a thickness t2 of 38 μm.

The circuit substrate 25 was inserted into the concave portion 17. They were bonded on the first electrode 9 and second electrode 10, respectively, using a conductive adhesive as the adhesive member 26.

A reliability test was conducted on eight different ultrasonic probes 1 produced and bonded with the circuit substrate 25 formed in the aforementioned procedure, and the reliability was checked. In the present embodiment, L2/L1=L4/L3. Thus, eight different ultrasonic probes 1 each have L2/L1 values of 1.5%, 1.9%, 2.0%, 5%, 10%, 11% and 15%. Further, the lengths of the reception element layer 3 in the direction of elevation are 97%, 96.2%, 96%, 90%, 80%, 78% and 70% with respect to L1 or L4.

Comparative Example 1

In the Comparative Example, after the reception element layer 3 was formed in the same procedure as that of the Example. The layer was cut into a piece having a length of 10 mm in the X-axis direction and a length of 50 mm in the Y-axis direction. These pieces of the layer were used in this test. Further, the first electrode 9 and second electrode 10 were formed to have a length of 20 mm in the X-axis direction. Otherwise, the components have the same structure as that of the Example. Thus, the same procedure was used in the step of lamination and bonding to produce a reception element layer 3.

After lamination, the portions projected from the first electrode 9 and second electrode 10 of the reception element layer 3 were bonded on the organic piezoelectric elements 21 and 22 of the circuit substrate 25, using a conductive adhesive. Thus, a hundred ultrasonic probes 1 were manufactured. In the Comparative Example, L2/L1 was 0%.

[Test Procedure]

The ultrasonic probe 1 manufactured on a tentative basis and the ultrasonic probe 1 in the Comparative Example were placed on a shaker table and were put to a vibration test. After the test, 15 MHz ultrasonic waves were sent from the ultrasonic wave transmitter toward the ultrasonic probes 1 of the Example and Comparative Example. The level of the signal received by the reception element layer 3 was measured from the terminal of the circuit substrate 25. The ultrasonic probe 1 was rejected in the test if the signal level did not exceed 20% of the specified voltage. Thus, rejection rates in the Example and Comparative Example were calculated under the respective conditions.

[Test Result]

Table 1 illustrates the result of the test.

TABLE 1

|  | Comparative Example | Example | | | | | | |
| --- | --- | --- | --- | --- | --- | --- | --- | --- |
| L2/L1 (%) | 0 | 1.5 | 1.9 | 2 | 5 | 10 | 11 | 15 |
| Rejection rate (%) | 35 | 4 | 2 | 0 | 0 | 0 | 0 | 0 |

In the Example, the rejection rate did not exceed 5%, exhibiting a sharp contrast to the Comparative Example wherein the rejection rate marked a high level of 35%. Hence the reliability was enhanced. Further, in the Example wherein the L2/L1 was 2% or more, the rejection rate was 0%, which demonstrates a drastic improvement in reliability.

Further, it has been verified that a prescribed level of received signal can be obtained if the length of the reception element layer 3 in the direction of elevation is 80% or more with respect to L1 or L4.

As described above, the present invention provides an ultrasonic probe capable of ensuring highly reliable connection of the electrode of the piezoelectric element and wiring member, and an ultrasonic diagnostic device equipped with a highly reliable ultrasonic probe.

| DESCRIPTION OF REFERENCE NUMERALS | |
| --- | --- |
| 1. | Ultrasonic probe |
| 2. | Transmission element |
| 3. | Reception element |
| 5. | Packing material |
| 6. | Matching layer |
| 9. | First electrode |
| 10. | Second electrode |
| 13. | Intermediate layer |
| 14. | Third electrode |
| 15. | Fourth electrode |
| 17. | Concave portion |
| 18, 19. | Projecting portions |
| 20. | Substrate material |
| 21, 22. | Conductive section |
| 23. | Cover lay |
| 24. | End face |
| 25. | Circuit substrate |
| 26. | Adhesive member |
| 31. | Ultrasonic diagnostic device proper |
| 33. | Cable |
| 41. | Operation input section |
| 42. | Transmission circuit |
| 43. | Reception circuit |
| 44. | Image processing section |
| 45. | Display section |
| 46. | Control section |
| 100. | Ultrasonic diagnostic device |

What is claimed is:

1. An ultrasonic probe comprising:

at least one transmission element layer for transmitting ultrasonic waves;

at least one reception element layer for receiving ultrasonic waves, wherein an electrode is provided on each of both surfaces opposed in a direction of a thickness of the reception element layer; and at least one matching layer for matching acoustic impedance;

wherein the transmission element layer, the reception element layer, and the matching layer are arranged in this order in a direction of transmitting the ultrasonic waves, wherein an upper layer and a lower layer sandwiching the electrodes formed on both surfaces of the reception element layer are each provided with a projecting portion projecting from the reception element layer in a direction of elevation, wherein one of the electrodes formed on the reception element layer is formed so as to extend onto a surface of one of the projecting portions opposed to the upper layer, wherein the other of the electrodes formed on the reception element layer is formed so as to extend onto a surface of the other of the projecting portions opposed to the lower layer, and wherein the ultrasonic probe further comprises:

a circuit substrate including conductive sections formed on each of both surfaces of a substrate member of the circuit substrate, wherein the surfaces are perpendicular to a direction of a thickness of the substrate member, and a concave portion surrounded by: (i) the electrode formed on the surface of the projecting portion of the upper layer, (ii) an end face of the reception element layer, and (iii) the electrode formed on the surface of the projecting portion of the lower layer, wherein at least a part of the circuit substrate is inserted into the concave portion; and wherein a first one of the conductive sections formed on one surface of the substrate member is connected to the electrode formed on the projecting portion of the upper layer, and a second one of the conductive sections formed on the other surface of the substrate member is connected to the electrode formed on the projecting portion of the lower layer.

2. The ultrasonic probe of claim 1, wherein surfaces of the substrate member, which are opposed to each other in the direction of the thickness of the substrate member and which are at an end portion of the circuit substrate and inserted into the concave portion, are not covered with the conductive sections.

3. The ultrasonic probe of claim 1, wherein a length of the projecting portion of the upper layer in the direction of elevation is 2% or more of a length of the upper layer in the direction of elevation;

wherein a length of the projecting portion of the lower layer is 2% or more of a length of the lower layer in the direction of elevation; and wherein a length of the reception element layer is 80% or more of each of the lengths of the upper and lower layers in the direction of elevation.

4. The ultrasonic probe of claim 1, wherein a thickness of the circuit substrate with portions of the conductive sections inserted into the concave portion is 80% or more and less than 100% of the thickness of the reception element layer.

5. An ultrasonic diagnostic device provided with the ultrasonic probe of claim 1.

6. The ultrasonic probe of claim 1, wherein the upper layer is the matching layer, and the lower layer is the transmission element layer.

7. The ultrasonic probe of claim 1, further comprising an intermediate layer which is provided between the reception element layer and the transmission element layer, wherein the transmission element layer, the intermediate layer, the reception element layer, and the matching layer are arranged in this order in the direction of transmitting the ultrasonic waves.

8. The ultrasonic probe of claim 7, wherein the upper layer is the matching layer, and the lower layer is the intermediate layer.

9. The ultrasonic probe of claim 1, wherein the first one of the conductive sections is connected to the electrode formed on the projecting portion of the upper layer and the second one of the conductive sections is connected to the electrode formed on the projecting portion of the lower layer, using a conductive adhesive member.

10. The ultrasonic probe of claim 1, wherein the upper layer and the lower layer are provided with projecting portions on both sides of the reception element layer so as to project from the reception element layer in the direction of elevation on both sides.

11. The ultrasonic probe of claim 10, wherein concave portions are provided on both sides of the reception element layer in the direction of elevation, and wherein the circuit substrate is inserted into the concave portions and connected to the electrodes formed on the projecting portions on both sides of the reception element layer in the direction of elevation.

* * * * *